United States Patent
Prins et al.

[11] Patent Number: 5,891,732
[45] Date of Patent: Apr. 6, 1999

[54] METHOD FOR DETERMINING FOAMING BEHAVIOR OF A LIQUID

[75] Inventors: Albertus Prins, Wageningen; Rudi Leendert de Jong, Alphen a/d Rijn, both of Netherlands

[73] Assignee: Heineken Technical Services B.V., Amsterdam, Netherlands

[21] Appl. No.: 860,907

[22] PCT Filed: Jan. 11, 1996

[86] PCT No.: PCT/NL96/00026

§ 371 Date: Aug. 27, 1997

§ 102(e) Date: Aug. 27, 1997

[87] PCT Pub. No.: WO96/21860

PCT Pub. Date: Jul. 18, 1996

[30] Foreign Application Priority Data

Jan. 13, 1995 [NL] Netherlands ............... 9500079

[51] Int. Cl.⁶ .................................................. G01N 33/14
[52] U.S. Cl. .................... 436/24; 73/60.11; 426/477; 436/20; 436/22; 436/164; 436/168
[58] Field of Search ................... 436/22, 20, 24, 436/164, 166, 167, 168; 99/323.1; 426/564, 569, 477; 73/60.11

[56] References Cited

U.S. PATENT DOCUMENTS

| 589,065 | 8/1897 | Zwietusch | 426/477 |
| 4,204,962 | 5/1980 | Ford . | |
| 4,677,304 | 6/1987 | Camp et al. | 250/577 |
| 5,021,250 | 6/1991 | Ferguson | 426/231 |
| 5,451,104 | 9/1995 | Kleen et al. | 422/133 |
| 5,597,950 | 1/1997 | Mullen | 73/60.11 |

FOREIGN PATENT DOCUMENTS

| 2158574 | 11/1995 | United Kingdom . |
| WO 93/02783 | 2/1993 | WIPO . |

*Primary Examiner*—Jan Ludlow
*Attorney, Agent, or Firm*—Pearne, Gordon, McCoy & Granger LLP

[57] ABSTRACT

The invention relates to a method for determining foaming behavior of a liquid by use of a gas, which includes supplying the gas to an amount of the substantially gas-free liquid to form a foam and analyzing one or more properties of the foam, wherein the gas is supplied through a grid provided with holes having a diameter of 25 to 100 μm, which holes are located at a mutual distance of 5 to 15 times the diameter of the holes.

18 Claims, 3 Drawing Sheets

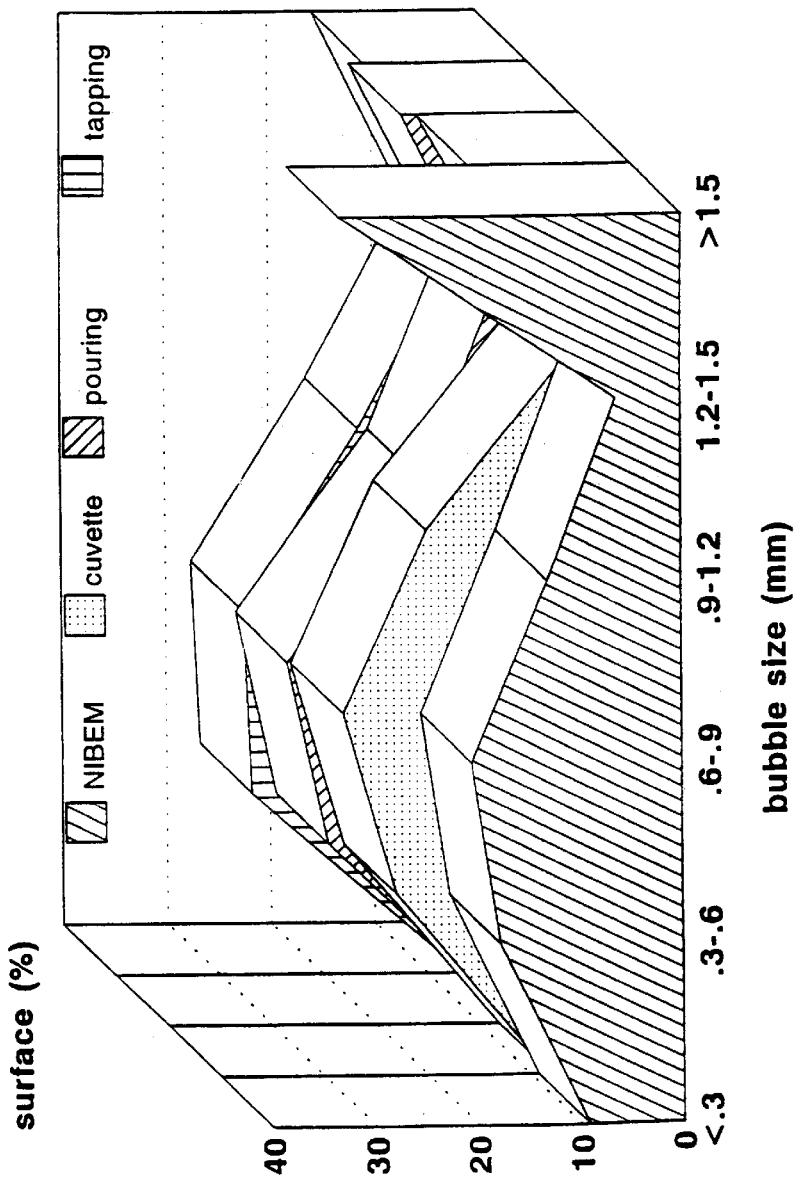

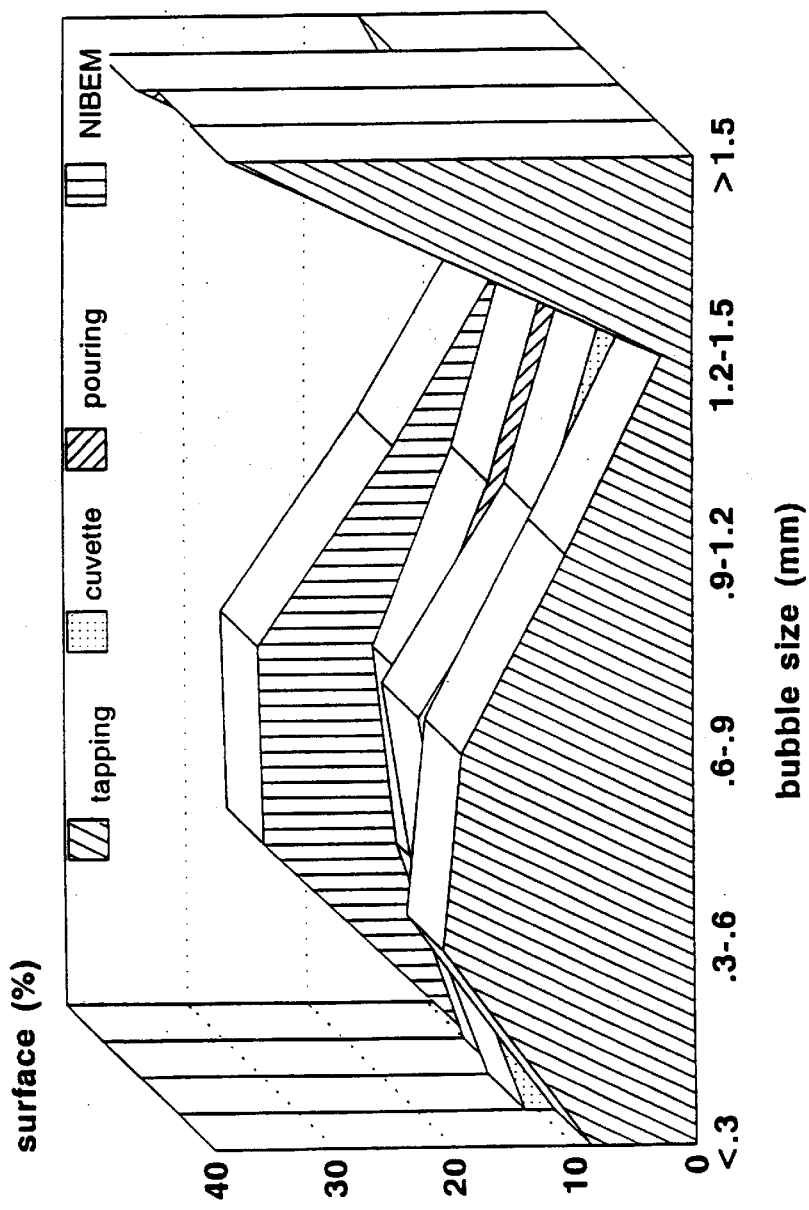

METHOD FOR DETERMINING FOAMING BEHAVIOR OF A LIQUID

FIELD OF THE INVENTION

The present invention relates to a method for determining the foaming behaviour (foaming analysis) of a liquid. More in particular, the invention relates to a method for reliably simulating in an analysis the practical situation of foaming of a beverage so that by means of a small amount of material the behaviour in daily practice can be predicted.

DESCRIPTION OF THE RELATED ART

In general, it is important to be able to determine the foaming behaviour of liquids that show any form of foaming behaviour. In the first place, this applies to gaseous beverages, but also for other, gaseous or nongaseous, liquids, it may be important to determine the behaviour of the foam. Examples of such liquids, except the above-mentioned gaseous beverages, are other gaseous liquids, but also solutions of components capable of giving a foam, such as detergents. It may also be of importance to the examination of foam-stabilizing or foam-inhibiting additives.

When judging of the quality of carbonated beverages, the properties of the foam are a very important factor. This is in particular the case with beer, but also in soft drinks (including the so-called "sports drinks"), cola, carbonated milk products, wine and champagne the behaviour of the foam plays a great part in the judgment of the quality of the product.

One aspect of the quality of the foam in beer is concerned with the foam height and the rate of the decrease of the foam height. This decrease is caused by drainage, coalescence and disproportionation. The bubble size distribution is of essential importance to the rate of the development of thoses processes.

When judging of the foam quality of beer, it seems most obvious to pour the beverage by hand or with an automatic pouring or tapping device. However, these methods are rather laborious, while, furthermore, much material is required for the analysis. Because of the drawbacks of this method other methods less laborious and requiring less material have been sought for.

At present the most current method for analysing foam is the use of a so-called "flasher". As shown in FIG. 1, the gaseous beverage, in this case beer, in a bottle 1 is pressed under the $CO_2$ pressure at which the bottle was filled, via a riser pipe 2 through a throttling port 3. Consequently, a pressure drop occurs immediately after the constriction (throttling port), which results in "flashing" of the beer. Thus foam is formed which is collected in a vessel 4 and is analysed. This analysis is conducted by means of a conventional "NIBEM" foaming analyser.

Another method developed in the course of time consists in introducing into a cuvette the liquid to be analysed, from which gas is substantially removed (in the case of beer: carbon dioxide), followed by introducing $CO_2$ into the liquid through a grid of sintered glass arranged in the bottom of the cuvelle: the so-called NIBEM method. Although a foam could thus be obtained, it turned out to be impossible in this way to predict the foaming behaviour of the liquid in practice, because the bubble size distribution could not be properly controlled.

For this reason, further researches were conducted into improvement of the analysis method, which has resulted in the insight that a reliable simulation of the practical situation can be obtained by generating the foam by means of a, preferably metal, grid provided with holes having a diameter of 25 to 100 $\mu$m, which holes are located at a mutual distance of 5 to 15 times the diameter of the holes.

SUMMARY OF THE INVENTION

The invention therefore relates in a first embodiment to a method for determining foaming behaviour of a liquid by means of a gas, which comprises supplying a gas to an amount of the substantially gas-free liquid to form a foam and analysing one or more properties of the foam, wherein the gas is supplied through a grid provided with holes having a diameter of 25 to 100 $\mu$m, which holes are located at a mutual distance of 5 to 15 times the diameter of the holes.

According to a second variant the invention relates to a method for generating foam in beer, which comprises supplying a gas approved for use in foods, in particular $CO_2$, to beer through a grid provided with holes having a diameter of 25 to 100 $\mu$m, which holes are located at a mutual distance of 5 to 15 times the diameter of the holes.

In this connection it is observed that WO-A 9302783 describes a method for generating foam, which method is particularly directed to foaming all kinds of building mortars. This method comprises introducing the air or $CO_2$ into a mixing chamber, through which the material to be foamed flows, which mixing chamber is provided with micropores (5 to 250 $\mu$m). According to this method there is obtained a foam having a narrow bubble size distribution. However, the method according to the invention is not concerned with obtaining a foam having a narrow bubble size distribution, but the foam quality should correspond to the practical situation in beer, for instance, this means that there should be a reasonable bubble size distribution.

DESCRIPTION OF PREFERRED EMBODIMENTS

Of special importance to the predicting value of the measurement is that there are:

1. an identical bubble size distribution,
2. an equal foam height, and
3. an identical moisture content of the foam, i.e. an equal gas fraction.

When carrying out the method according to the invention, it is preferred to make use of a, possibly thermostated, cuvette, a glass or a beer glass-shaped glass cuvette closed at the bottom side with a metal (preferably stainless steel) grid provided with holes having a diameter of 25 to 100 $\mu$m, which holes are located at a mutual distance of 5 to 15 times the diameter of the holes. Preferably, these holes have a diameter of 40 to 65 $\mu$m, the mutual distance of the holes preferably being 400 to 650 $\mu$m, i.e. a mutual distance of about ten times the diameter. The mutual distance of the holes is calculated as a centre-to-centre distance, there preferably being started from a regular distribution, e.g. a rhombic, triangular or square distribution. Of course, the mutual distance is only concerned with the nearest holes.

The liquid to be analysed is poured into the cuvette, gas first being removed from this liquid, if necessary. This may be done, e.g., by stirring the liquid for some time in the air. Subsequently, the gas is passed through the grid into the liquid. The rate and amount of the supply is important and can be determined by means of simple tests. After the foam has been formed, the foaming properties can be determined with the eye or by means of a foam analyser. Suitable parameters are, inter alia, the bubble size distribution, the changes in this distribution with time, and the decrease of the height of the foam head with time, the content of gas (gas fraction) and the rate of the liquid draining from the foam.

The method according to the invention can be used to analyse the foaming behaviour of gaseous or nongaseous liquids. The liquids to be analysed have already been enumerated in the introduction. In the analysis of the foaming behaviour of gaseous beverages there is preferably used the gas initially present in the liquid. As far as nongaseous liquids are concerned, efforts will be directed to using gases relevant in practice. In detergents this will often be air. In general, it can be said that all the gaseous substances and gas mixtures can be used that do not enter into reaction with the liquid to be analysed. Examples of such gases are carbon dioxide, air, nitrogen, and noble gases. In the analysis of products intended for consumption, the use of carbon dioxide gas or nitrogen gas is preferred.

Examples of beverages to be analysed are the conventional carbonated beverages, such as the various types of beer (standard, "light", low-alcohol, non-alcoholic, strong, dark, young beer, etc.), soft drinks, such as "up" and cola, and beverages with fruit flavour, but also the icotonic, hypotonic and hypertonic as well as energy-providing sports drinks, cola, sparkling wines, cider, champagne and carbonated milk drinks.

It has been found that the method according to the invention enables a reliable prediction of the foaming behaviour in practice. As compared to the conventional analysis methods, this method is very advantageous, because small amounts of material will suffice, about half a liter, while the apparatus is quite simple, certainly as compared to automatic tapping or pouring devices. A problem also occurring with the latter is that not all the types of bottles and other containers can be used therewith. Finally, it is also important that the apparatus is easy to clean and can be readily produced on a large scale, without measuring differences occurring between the various apparatuses.

The grid used in the method according to the invention is preferably of metal, more in particular stainless steel. Since the liquids to be analysed are in general not very corrosive, simple types of steel will suffice, e.g. 316 L, or comparable materials. The grids are made of a plate, e.g. by burning in, by means of a laser, the holes with the right diameter at the right place. By using a computer-controlled laser, it is possible to produce large series of completely identical grids. This has the advantage that grids can be replaced without causing problems, without affecting the results of the analysis.

BRIEF DESCRIPTION OF THE DRAWINGS

The invention will be explained with reference to the drawings, in which.

The invention will be illustrated with reference to some examples, which show that the results of foaming according to the method of the invention give a reliable prediction of the behaviour in practice.

EXAMPLE

By means of a so-called foam analyser the bubble size distribution has been determined in beer foamed in a number of different ways. The foam analyser consists of a measuring electrode, an optical unit, and a calculating unit.

The measuring electrode is provided with a 20 $\mu$m optical quartz fibre, through which light from the optical unit is passed. The measuring electrode is moved through the foam to be analysed for 1 sec over a distance of 10 cm, and the reflected light is received in the optical unit, in which the incident light is separated from the reflected light. The reflected light is detected in the optical unit, after which the signal is read in by the computer. On the basis of a statistical analysis of the reflected light an insight is gained into the bubble size distribution of the foam.

Figure 1:
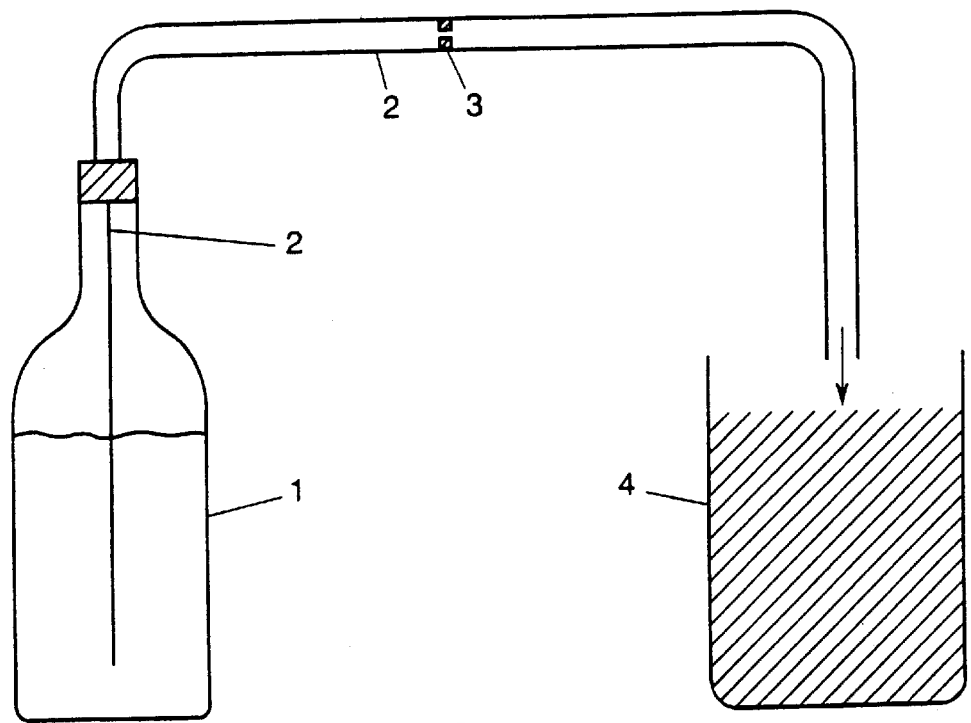
FIG. 1 shows a conventional analysis method and FIG. 2 the method according to the invention.
Figure 2:
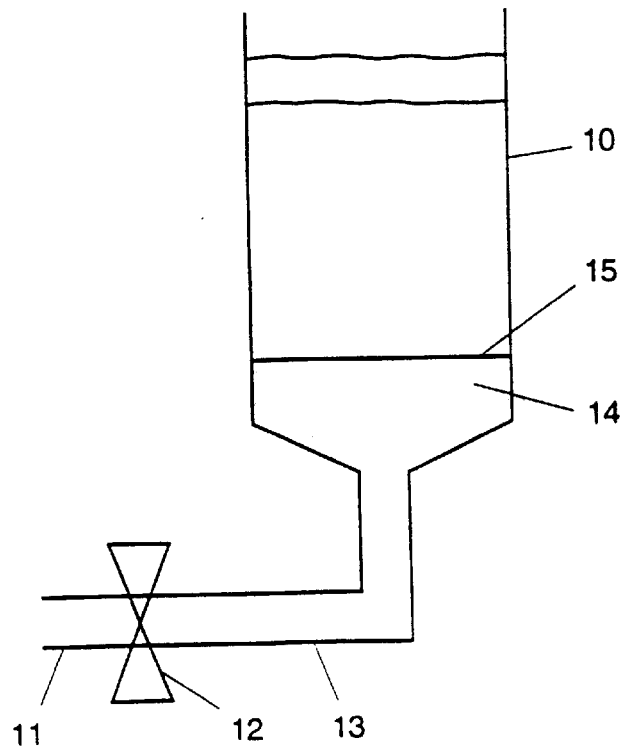
FIG. 2 shows a cuvette 10, into which degassed beer can be introduced. Through conduit 11, valve 12 and conduit 13 the gas is introduced into the space 14 below the grid 15 in a closely determined amount and at a controlled rate, while generating a foam in the liquid through the holes in the grid 15. This foam is then analysed by means of an analysis apparatus, not shown.

FIGS. 3 and 4 show the bubble size distribution determined by means of the foam analyser for four foams at two times. These foam types are: foam according to the invention (cuvette); draught beer (tapping); NIBEM foam (NIBEM); and foam from an automatic pouring device (pouring). In the system according to the invention there is used an apparatus, as shown in FIG. 2, in which the grid is a stainless steel plate provided with holes having a diameter of 45 $\mu$m, at a mutual distance of 500 $\mu$m, arranged in a "square" pattern.

FIG. 3 shows that almost immediately after generating the foam the NIBEM foam shows a clearly different distribution, which, inter alia, is to be ascribed to the fact that it is "very" wet, i.e. it has a high liquid content, namely 40% versus 10% for the other foams. Because in the measuring method the small bubbles of such a wet foam are not "seen" sufficiently, the distribution obtained for the NIBEM foam is unreliable.

In the course of time each foam will become drier by drainage, so that the measurement of the NIBEM foam becomes more reliable as well.

FIG. 4, a measurement after three minutes, shows that the NIBEM foam is more stable than the practical foams and is also more stable than the foam obtained according to the invention.

It has therefore been found that the method according to the invention provides a distribution rather close to practice, while the other analysis method, using a grid of sintered glass, gives no reliable measurement.

What is claimed is:

1. Method for determining foaming behaviour of a liquid by means of a gas, which comprises supplying the gas to an amount of a substantially gas-free liquid to form a foam and analyzing one or more properties of the foam, wherein the gas is supplied through a grid provided with holes having a diameter of 25 to 100 $\mu$m, which holes are located at a center-to-center distance of 5 to 15 times the diameter of the holes.

2. Method according to claim 1, wherein the liquid to be analysed is introduced into a thermostated cuvette, provided at the bottom side with said grid.

3. Method according to claim 1, wherein the liquid to be analysed is a carbonated liquid, from which carbon dioxide is substantially removed prior to the analysis.

4. Method according to claim 1, wherein the liquid is selected from the group consisting of alcoholic and non-alcoholic beverages.

5. Method according to claim 1, wherein the liquid is selected from the group consisting of beer, low-alcohol beer, non-alcoholic beer, soft drinks, cola, milk products which are beverages, wine, and champagne.

6. Method according to claim 1, wherein the center-to-center distance of the holes is between 400 to 650 $\mu$m.

7. Method according to claim 6, wherein the liquid to be analysed is a carbonated liquid, from which carbon dioxide is substantially removed prior to the analysis.

8. Method according to claim 6, wherein the liquid is selected from the group consisting of alcoholic and non-alcoholic beverages.

9. Method according to claim 6, wherein the liquid is selected from the group consisting of beer, low-alcohol beer, non-alcoholic beer, soft drinks, cola, milk products which are beverages, wine, and champagne.

10. Method according to claim 1, wherein the diameter of the holes is between 40 and 65 $\mu$m.

11. Method according to claim 10, wherein the liquid to be analysed is a carbonated liquid, from which carbon dioxide is substantially removed prior to the analysis.

12. Method according to claim 10, wherein the liquid is selected from the group consisting of alcoholic and non-alcoholic beverages.

13. Method according to claim 10, wherein the liquid is selected from the group consisting of beer, low-alcohol beer, non-alcoholic beer, soft drinks, cola, milk products which are beverages, wine, and champagne.

14. Method according to claim 10, wherein the center-to-center distance of the holes is between 400 to 650 $\mu$m.

15. Method according to claim 14, wherein the liquid to be analysed is a carbonated liquid, from which carbon dioxide is substantially removed prior to the analysis.

16. Method according to claim 14, wherein the liquid is selected from the group consisting of alcoholic and non-alcoholic beverages.

17. Method according to claim 14, wherein the liquid is selected from the group consisting of beer, low-alcohol beer, non-alcoholic beer, soft drinks, cola, milk products which are beverages, wine, and champagne.

18. Method for generating foam in beer, which comprises supplying $CO_2$ to beer through a grid provided with holes having a diameter of 25 to 100 $\mu$m, which holes are located at a center-to-center distance of 5 to 15 times the diameter of the holes.

* * * * *